(12) United States Patent
Härer et al.

(10) Patent No.: US 8,126,236 B2
(45) Date of Patent: Feb. 28, 2012

(54) METHOD AND DEVICE FOR THE SEPARATE THREE-DIMENSIONAL REPRESENTATION OF ARTERIES AND VEINS IN AN EXAMINATION OBJECT AND DEVICE

(75) Inventors: Wolfgang Härer, Erlangen (DE); Michael Zellerhoff, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 834 days.

(21) Appl. No.: 12/283,419

(22) Filed: Sep. 11, 2008

(65) Prior Publication Data
US 2009/0080736 A1 Mar. 26, 2009

(30) Foreign Application Priority Data
Sep. 21, 2007 (DE) .......................... 10 2007 045 313

(51) Int. Cl.
*A61B 6/03* (2006.01)
(52) U.S. Cl. ..................... 382/130; 382/131; 378/98.12; 378/901
(58) Field of Classification Search .................. 382/130, 382/131, 154, 260–265; 378/4, 8, 901, 98.12
See application file for complete search history.

(56) References Cited

U.S. PATENT DOCUMENTS

| | | | | |
|---|---|---|---|---|
| 5,978,439 | A * | 11/1999 | Koppe et al. ...................... | 378/8 |
| 6,983,182 | B2 * | 1/2006 | Mistretta ........................ | 600/425 |
| 7,519,412 | B2 * | 4/2009 | Mistretta ........................ | 600/407 |
| 7,545,901 | B2 * | 6/2009 | Mistretta ........................... | 378/4 |
| 7,558,372 | B2 * | 7/2009 | Zellerhoff .................. | 378/98.12 |
| 7,702,074 | B2 * | 4/2010 | Sakaguchi et al. .......... | 378/98.12 |
| 2007/0232901 | A1 | 10/2007 | Benndorf et al. | |

FOREIGN PATENT DOCUMENTS
DE 10 2006 012 181 A1 9/2007

OTHER PUBLICATIONS

Masato Matsumoto et al., "3D CT Arteriography and 3D-CT Veneography: The Separate Demonstration of Arterial-Phase and Venous-Phase on 3D CT Angiography in a Single Procedure," AJAR Am J Neuroradiol 26:635-641, Mar. 2005.*
C.A. Mistretta et al., "Highly Constrained Backprojection for Time-Resolved MRI", Magnetic Resonance in Medicine 55, 2006, pp. 30-40.
M. Supanich et al., "Factor of Ten Dose Reduction in CT Perfusion Imaging", Medical Physics, Jun. 2006, pp. 2279, vol. 33, Issue 6.
Huang et al.; "HYPR Signal Behavior in Time-Resolved MR Angiography", International MRA Club, 18th Annual Conference, MR Angiography, Sep. 13-15, 2006, Biozentrum, University Basel, Switzerland, Proc., pp. 30.

* cited by examiner

*Primary Examiner* — Allen C. Ho

(57) ABSTRACT

Method for three-dimensional representation of arteries and/or veins in an object by a tomography x-ray device is proposed. A mask pass with N projections at N angular positions without contrast agent is implemented. A first filler pass with M projections at M angular positions after injecting a contrast agent, where M<N is implemented, followed by a second filler pass with N−M projections at N−M angular positions. A composite three-dimensional volume data record is reconstructed from an intermediate data record determined from the mask pass, the first and the second filler pass. A reprojection for arteries and/or for veins is calculated by reprojection of the first filler pass and/or of the second filler pass from the composite three-dimensional volume data record. A three-dimensional volume data record for arteries and/or for veins is calculated by weighting the composite three-dimensional volume data record taking into account the respective measured and calculated projection images.

20 Claims, 2 Drawing Sheets

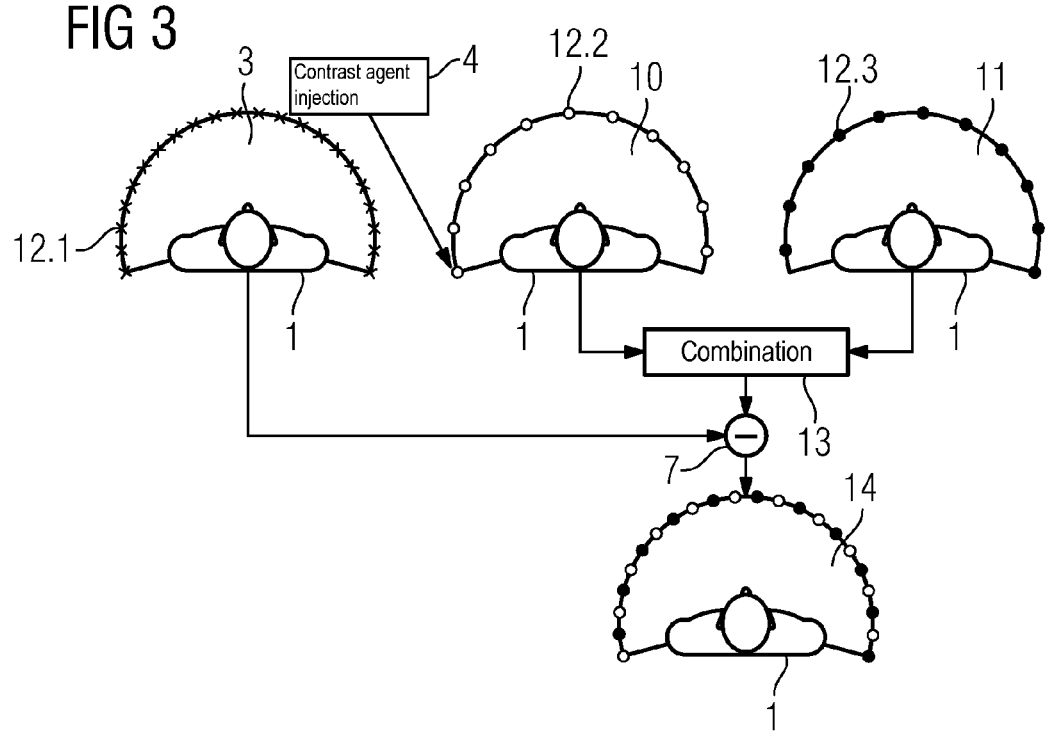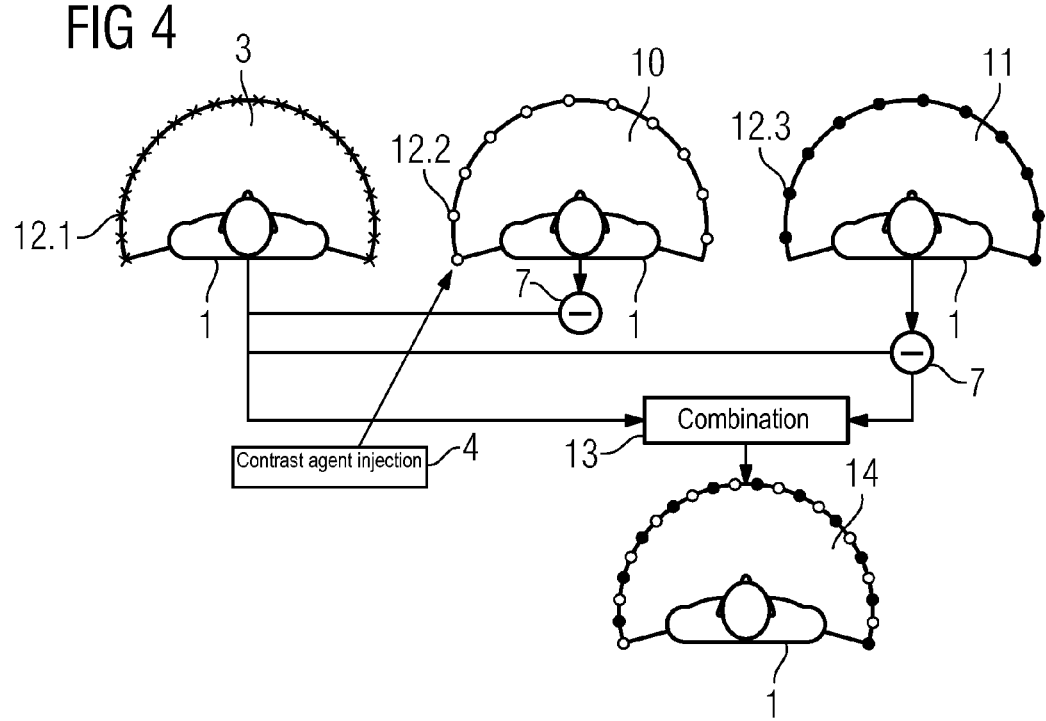

METHOD AND DEVICE FOR THE SEPARATE THREE-DIMENSIONAL REPRESENTATION OF ARTERIES AND VEINS IN AN EXAMINATION OBJECT AND DEVICE

CROSS REFERENCE TO RELATED APPLICATIONS

This application claims priority of German application No. 10 2007 045 313.4 DE filed Sep. 21, 2007, which is incorporated by reference herein in its entirety.

FIELD OF INVENTION

The present invention relates to a method for the separate three-dimensional representation of arteries and/or veins of a vascular system in an examination object by means of a tomography x-ray device and a device, in particular for executing the method. The invention is preferably applied in C-arm angiographs.

BACKGROUND OF INVENTION

There is an increasing demand for the most accurate possible three-dimensional representation of the appearance and pattern of vessels in parts of the body, in particular of arteries and veins, for diagnostic purposes within the field of vascular diseases and the therapy thereof. The examination of cerebral aneurysms represents an important field of application; this also includes an analysis and optimal representation for defining the aneurysm neck using topographical relationships with adjacent vessels. Angiographs are also carried out on other parts of the body, in order to determine arteriosclerotic changes or deformities. The introduction of computer-aided rotation angiography, which reconstructs three-dimensional representations with an equal resolution from the projection raw data, achieves a technical breakthrough within the field of diagnostics.

So-called C-arm angiographs form the prior art here, in which an x-ray source and a sensor arranged opposite thereto are rotated about the part of the body of a patient to be examined in an arc encompassing approximately 200° with between 50 and 500 x-ray images being recorded and digitally stored in the process. A three-dimensional model of the x-rayed part of the body can be calculated from the projection x-ray images recorded from different projection angles. Conventional 3D angiography nevertheless fails to ensure adequately clear separation between the arterial and venous vascular systems, by virtue of the recording times and the dynamics of contrast agent propagation.

With the already known three-dimensional vascular representation, a so-called mask pass and a filler pass are recorded. During the mask pass the C-arm rotates about the examination object and x-ray images are recorded over the predetermined angular range. A contrast agent is then injected into the vessel of interest and with another C-arm rotation, the so-called filler pass, a second set of x-ray images is recorded. The projection data of both image sequences is now subtracted from one other such that only the contrasted vessels (i.e. containing contrast agent) can still be seen in the result. These are now reconstructed to form a three-dimensional data record using a 3D reconstruction method. Alternatively masks and filler pass data can also be reconstructed separately and the resulting three-dimensional data records subtracted from one another.

The 3D angiography method according to the prior art generally provides a three-dimensional data record, which represents both a part of the arterial vascular system as well also as parts of the venous vascular system. The reason for this shortcoming in current angiography systems can be attributed to the rotation time of the tomograph of around 5 s being significantly longer than the so-called arterial phase of vascular contrasting, which only lasts 2 to 3 seconds. The contrast agent then migrates via the usual capillary paths into the venous vascular system so that a venous phase of the vascular contrasting is shown after the arterial phase has passed, said vascular contrasting being recorded in a subsequent part of the rotation of the tomograph, thereby resulting in a three-dimensional mixed structure of arteries and veins.

SUMMARY OF INVENTION

An object underlying the present invention is thus to provide a particularly fast and simple method, which is suitable for generating three-dimensional data records of vessels, which represent either only arteries or only veins, depending on requirements.

According to the invention this object is achieved by the method for the separate three-dimensional representation of arteries and/or veins as claimed in an independent claim as well as the device for separate three-dimensional representation as claimed in a further independent claim; advantageous embodiments, aspects and details of the present invention result from the dependent claims, the description and the appended drawings.

The idea underlying the invention is to implement two fast filler passes for the separate representation of arteries and veins, with in each only some, ideally half, of the angular positions of the mask pass being used, so that a single injection of contrast agent is sufficient to record both the arterial phase (during the first filler pass) and also the venous phase of vascular contrasting (during the second filler pass).

Because it is possible to limit the number of injections of contrast agent to one, the load on the patient due to contrast agent is relatively low. The method can also be coordinated temporally in a simple manner in that the arterial phase and venous phase are each allocated to one filler pass. The patient is also subjected to a relatively low x-ray dose, as the number of x-ray recordings remains relatively small. The short recording time means that patients have to hold their breath and remain motionless for a shorter time and the treatment is therefore less unpleasant. The smaller number of projection recordings per filler pass is then offset by a weighting, which means that the quality of the three-dimensionally reconstructed volumes of the veins and arteries is at least comparable to those of double the number of recordings.

The inventive method for the separate three-dimensional representation of arteries and/or veins of a vascular system in an examination object by means of a tomography x-ray device comprises the following steps:
(a) Implementation of a mask pass of the x-ray device with N projections at N angular positions about the examination object without contrast agent;
(b) Implementation of a first filler pass of the x-ray device about the examination object with M projections at M of the N angular positions after injection of a contrast agent, where M<N;
(c) Implementation of a second filler pass of the x-ray device about the examination object with N–M projections an N–M of the N angular positions directly following the first filler pass;
(d) Reconstruction of a composite three-dimensional volume data record from an intermediate data record, said intermediate data record being determined from the data records resulting from the mask pass, the first filler pass and the second filler pass by subtraction and combination;

(e) Calculation of a reprojection data record for arteries by reprojection of the angular positions of the first filler pass from the composite three-dimensional volume data record and/or calculation of a reprojection data record for veins by reprojection of the angular positions of the second filler pass from the composite three-dimensional volume data record;

(f) Calculation of a three-dimensional volume data record for arteries and/or a three-dimensional volume data record for veins by weighting the composite three-dimensional volume data record taking into account the respective measured and the respective calculated projection images.

A tomography x-ray device here is understood to be an x-ray device, which uses an imaging method with calculation of a three-dimensional model of the examination object.

In the context of the present invention a mask pass is the pass of the tomography x-ray device without the use of a contrast agent.

As is commonly understood by those skilled in the art, a contrast agent is a substance, which is impermeable for the respective imaging method, in the present instance x-rays, and thus makes filled pole structures visible by a clear x-ray shadow.

A filler pass is understood to mean a pass of the tomography x-ray device, in which the cavity to be examined, in this instance vessels, is filled with a contrast agent to such a degree that an adequate contrast results in the imaging method.

A combination of data from the filler passes to form data records is understood to mean that sub-quantities of the data of the individual filler passes is combined to form a new data record according to predetermined rules, with the aid of a predetermined algorithm and if necessary with the input of a human evaluator.

The subtraction of data records, according to the normal use of this expression by those skilled in the art in respect of tomographic methods, is understood to be an computational procedure, in which measured data of a background is deducted from the measured data of interest in such a manner that essentially only the measured data of interest remains in the data record.

In order to generate a three-dimensional model from the projection image data of the individual recordings of the passes, a method is used, which is referred to as reconstruction in the field of angiography. This reconstruction generally includes filtering and backprojection.

One important field of application of the invention is the location of aneurysms in the vessels of the brain. It is however evident that the method according to the invention can in principle also be applied to other body parts of humans and other types of animal with a vascular system.

According to one embodiment of the invention M=N/2. This has the advantage for example that each of the two filler passes has the same number of projection images, so that arteries and veins can ultimately be reconstructed with the same quality. In this context it is also particularly advantageous to use every second angular position of the mask pass for the first filler pass and the remaining angular positions of the mask pass for the second filler pass, so that there is even distribution of the projection angles between the first and second filler passes. In particular the first filler pass is also started at the time of injection of the contrast agent into the vessels to be examined and the second filler pass is started at the start of the venous phase.

The weighting of the composite three-dimensional volume data record taking into account the respective measured and the respective calculated projection images can be realized in two different ways, both based on the so-called HYPR method.

According to a first alternative of the invention for step f) the volume data record for arteries is obtained by multiplying the composite three-dimensional data record by the backprojection of a weighted projection data record for arteries, with the weighted projection data record for arteries being formed from the quotients of the individual projection images of the first filler pass with the respective projection images of the reprojection data record for arteries produced for corresponding angular positions. The volume data record for veins is obtained in a comparable manner for step f), by multiplying the composite three-dimensional data record by the backprojection of a weighted projection data record for veins, with the weighted projection data record for veins being formed from the quotients of the individual projection images of the second filler pass with the respective projection images of the reprojection data record for veins produced for corresponding angular positions.

According to a second alternative of the invention the volume data record for arteries is obtained for step f) by multiplying the composite three-dimensional data record by the backprojection of the projection images of the first filler pass and then dividing it by the backprojection of the reprojection data record for arteries. Correspondingly the volume data record for veins is obtained for step f) by multiplying the composite three-dimensional data record by the backprojection of the projection images of the second filler pass and then dividing it by the backprojection of the reprojection data record for veins.

Use of the so-called HYPR method means that the number of projection images required for reconstruction of the arteries and veins for a good quality of the reconstructed volumes is significantly smaller than for a standard separate backprojection. The HYPR method is known in particular from magnetic resonance tomography, see for example the publication "Highly Constrained Backprojection for Time-Resolved MRI", by C. A. Mistretta et al., Magnetic Resonance in Medicine 55, 2006, page 30 ff.

The intermediate data record, which is reconstructed after the composite three-dimensional volume data record, can be obtained according to two different possibilities of equal value. The first possibility is that the intermediate data record results from Subtraction of part of the data record obtained during the mask pass, in which part the angular positions correspond to those of the first filler pass, from the data record of the first filler pass to form a first data record, Subtraction of part of the data record obtained during the mask pass, in which part the angular positions correspond to those of the second filler pass, from the data record of the second filler pass to form a second data record, and Combination of the first and second data records.

The second possibility is that the intermediate data record results from

Combination of the data records resulting from the first filler pass and the second filler pass to form a combined data record, Subtraction of the data record resulting from the mask pass from the combined data record taking into account corresponding angular positions.

According to a further embodiment of the invention the tomography x-ray device is formed by a C-arm x-ray device. Such C-arm x-ray devices are able to produce projection images as they circle quickly about a patient, having the advantage that with their relatively small form compared with a CT device, they still ensure easy access to the patient. C-arms supported on industrial robots in particular are extremely flexible.

Depending on the tomography x-ray device used and its movement pattern, in a preferred embodiment of the invention the mask pass, the first filler pass and the second filler pass are implemented in the same scan direction. In the case of tomography x-ray devices, which can change the scan easily, in other words the C-arm x-ray device for example, the mask pass, the first filler pass and the second filler pass are implemented in an alternating manner in different scan directions. It is possible to save time in this manner, as the x-ray device does not have to be returned to its original position to start the first filler pass and the second filler pass.

In a further aspect the invention is directed toward a device, with all that has been said in relation to the method also applying to the device or vice versa, so that references alternate. The inventive device is suitable for implementation of the inventive method. In one embodiment of the invention the tomography x-ray device is configured as a C-arm x-ray device.

BRIEF DESCRIPTION OF THE DRAWINGS

The invention and further advantageous embodiments according to features of the subclaims are described in more detail below with reference to schematic diagrams of exemplary embodiments in the drawing, without thereby restricting the invention to said exemplary embodiments. In the drawing:

FIG. 2 shows an inventive method for the separate representation of arteries and veins of a vascular system of examination object;

FIG. 3 shows a principle of the scanning of an examination object in a first embodiment; and FIG. 4 shows a principle of the scanning of an examination object in a second embodiment.

DETAILED DESCRIPTION OF INVENTION

Figure 1:
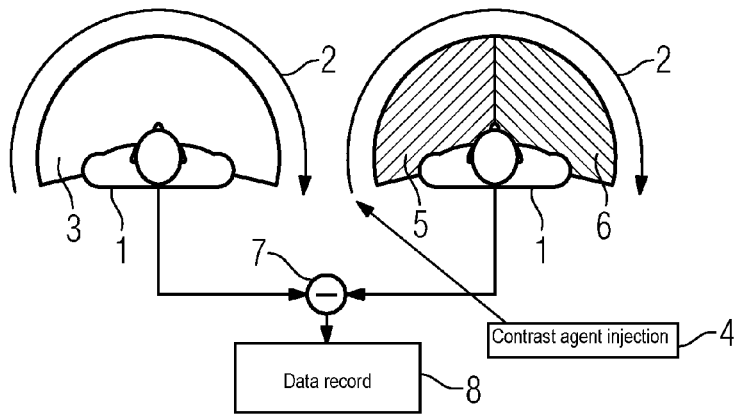
FIG. 1 shows a principle of the scanning of an examination object according to the prior art.
Figure 1:
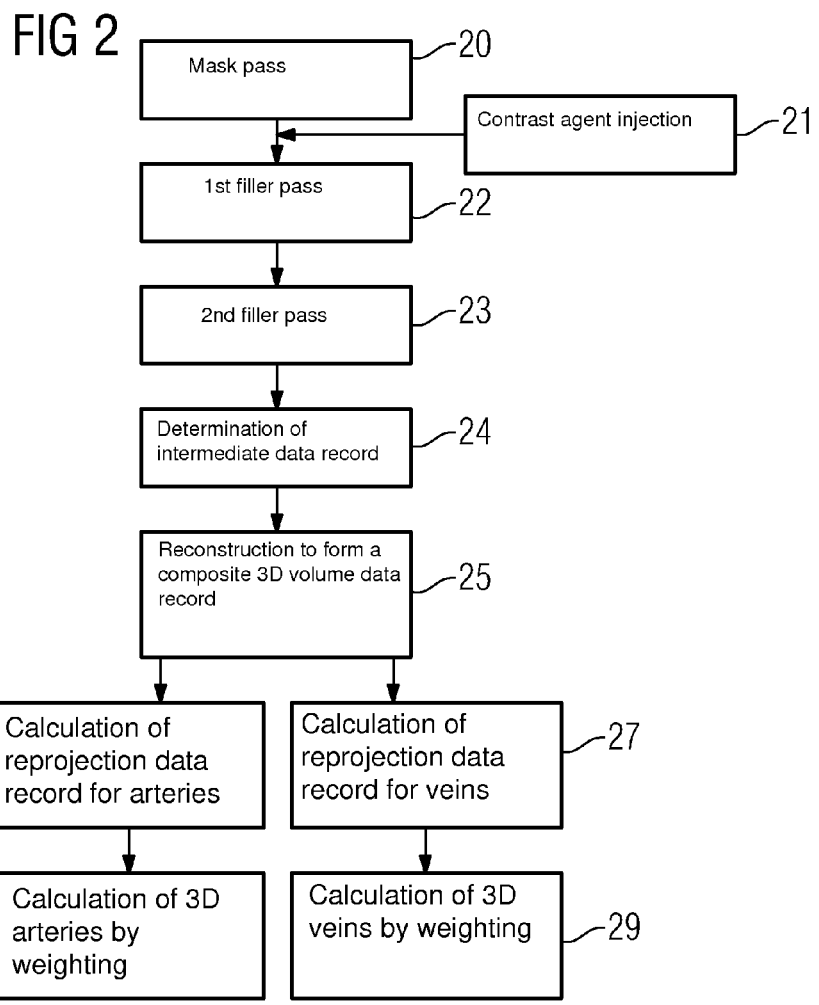

FIG. 1 shows the principle of the scanning of an examination object 1 according to the prior art. During a mask pass 3 a series of projection images is produced by a recording system circling 2 about an examination object, being recorded from an angular range of approximately 200°. The projection images are in particular recorded by a C-arm x-ray device, on which an x-ray source and an x-ray detector are permanently arranged. A contrast agent is then injected into the vascular system of interest by means of a contrast agent injection 4 and a so-called filler pass is then carried out. This filler pass contains the same number of projection images as the mask pass, which were likewise recorded at the same angular positions as during the mask pass.

Since in general the rotation time of such a C-arm is around 5 seconds, if a sufficient number of recordings are to be produced for a high-quality reconstruction but the arterial phase 5 of vascular contrasting only lasts around 2 to 3 seconds, with a method according to the prior art the arterial phase 5 and the venous phase 6 can only be represented at the same time. After the mask pass and filler pass have been recorded, a subtraction 7 takes place, in which the projection images of the mask pass are deducted from the projection images of the filler pass. This gives a data record 8, which is reconstructed using standard reconstruction methods to form a three-dimensional volume data record. Such standard reconstruction methods generally include filtering and backprojection of the data. The resulting three-dimensional volume data record represents arteries and veins at the same time.

The inventive method allows a separate three-dimensional representation of arteries and veins of a vascular system in an examination object. This is achieved in that two separate filler passes are implemented, each containing only half the number of projection images of the mask pass, but with the entire angular range being covered with both filler passes. This can be achieved for example by only going to every second angular position in the first filler pass and similarly going to every second angular position in the second filler pass, with the angular positions that were not used in the first filler pass being used here.

This scanning principle is shown in FIGS. 3 and 4. The mask pass 3 is effected at N different angular positions 12.1 about the examination object 1 (symbolized by the crosses), the first filler pass 10 at N/2 angular positions 12.2 (symbolized by the empty dots) and the second filler pass 11 at N/2 angular positions 12.3 (symbolized by the filled dots). N is preferably between 50 and 500 here. Before the start of the first filler pass 10 a contrast agent is injected into the examination object and in some instances there is a waiting period until the contrast agent reaches the vascular region to be examined. The second filler pass 11 takes place immediately after the first filler pass 10. Ideally the first filler pass lasts the same length of time as the arterial phase (generally around 2 to 3 s) of the vascular region and the second filler pass starts with the venous phase and lasts the same length of time as the venous phase (likewise around 2 to 3 s). Overall the two filler phases therefore take around 4 to 6 s.

Following the two filler passes—as shown in FIG. 3—a combination 13 of the data record of the first filler pass and the data record of the second filler pass is formed into a combined data record. A subtraction 7 of the data record of the mask pass from the combined data record is then carried out. The result is an intermediate data record 14 of projection images. A further possibility for obtaining this intermediate data record 14 is shown in FIG. 4. Here the corresponding projection images of the mask pass recorded at the same angular positions are deducted directly from the data record of the first filler pass. Likewise the corresponding projection images of the mask pass recorded at the same angular positions are deducted directly from the data record of the second filler pass. The two resulting data records are then combined so that the intermediate data record 14 is likewise obtained as a result.

An overview of the entire inventive method is shown in FIG. 2. The mask pass is carried out in a first step 20. After the second step 21, the injection of a contrast agent, in a third step 22 a first filler pass and in a fourth step 23 a second filler pass is carried out. In a fifth step 24 the intermediate data record is determined and in a sixth step 25 the intermediate data record is reconstructed to form a composite three-dimensional volume data record. Such a reconstruction generally includes filtering and backprojection and is referred to as a filtered backprojection. The composite three-dimensional volume data record thus obtained contains common data about the arteries and veins.

The following steps are carried out to obtain separate data about arteries and/or veins: In a seventh step 26 a reprojection data record for arteries is calculated. The two-dimensional reprojection data record for arteries is produced by reprojecting data from the composite three-dimensional volume data record respectively at the angular positions of the first filler pass, thus obtaining two-dimensional projection images again. In an eighth step 27 a two-dimensional reprojection data record for veins is calculated according to the same principle from the angular positions of the second filler pass and the composite three-dimensional volume data record. In a ninth step 28 a three-dimensional volume data record for arteries can then be calculated from the two-dimensional reprojection data record for arteries, from the first filler pass and from the composite three-dimensional volume data record by means of weighting. Similarly in a tenth step 29 a three-dimensional volume data record for veins is calculated from the two-dimensional reprojection data record for veins, from the second filler pass and from the composite three-dimensional volume data record by means of weighting.

Two alternatives can be used for the corresponding calculations of the ninth and tenth steps. The two variants are described below in an exemplary manner for arteries:

In a first alternative the two-dimensional data record of the first filler pass is divided by the two-dimensional reprojection data record for arteries. A new three-dimensional data record is then obtained from the resulting weighted reprojection data record for arteries by means of backprojection and this is multiplied by the composite three-dimensional volume data record. The result is a three-dimensional volume data record for arteries.

In a second alternative a backprojection of the two-dimensional data record of the first filler pass is calculated and a backprojection of the two-dimensional reprojection data record for arteries is then calculated. The two resulting three-dimensional data records are divided by one another and then multiplied by the composite three-dimensional volume data record. The result is likewise a three-dimensional volume data record for arteries.

Optionally a reconstruction of the data record obtained during the mask pass can also be calculated, so that a native three-dimensional volume data record can be obtained therefrom.

Using the inventive method allows the number of required projection images for the reconstruction of arteries and veins to be reduced significantly, in particular by the factor 2, compared with a method from the prior art. If it is assumed that a limited read-out rate of the x-ray detector represents the limiting variable for recording, it is thus possible to halve the duration of an examination.

The three rotation recordings, in other words the mask pass, and the two filler passes can be carried out either in the same rotation direction with fast backpasses between the recordings in each instance or in alternating rotation directions.

An inventive device for implementing the inventive method is provided for example by a C-arm x-ray device, whose C-arm is supported on an industrial robot, in particular a six-axis buckling arm robot, and can therefore be adjusted quickly and simply in all spatial directions.

The invention can be summarized briefly as follows: In order to be able to represent arteries and/or veins of a vascular system three-dimensionally, a method is provided for the separate three-dimensional representation of arteries and/or veins of a vascular system in an examination object by means of a tomography x-ray device with the following steps: implementation of a mask pass 3 of the x-ray device with N projections at N angular positions about the examination object 1 without contrast agent; implementation of a first filler pass 10 of the x-ray device about the examination object 1 with M projections at M of the N angular positions after injection of a contrast agent, where M<N; implementation of a second filler pass 11 of the x-ray device about the examination object 1 with N−M projections at N−M of the N angular positions directly following the first filler pass 10; reconstruction of a composite three-dimensional volume data record from an intermediate data record 14, said intermediate data record 14 being determined from the data records resulting from the mask pass 3, the first filler pass 10 and the second filler pass 11 by subtraction 7 and combination 13; calculation of a reprojection data record for arteries by reprojection of the angular positions of the first filler pass 10 from the composite three-dimensional volume data record and/or calculation of a reprojection data record for veins by reprojection of the angular positions of the second filler pass 11 from the composite three-dimensional volume data record; calculation of a three-dimensional volume data record for arteries and/or a three-dimensional volume data record for veins by weighting the composite three-dimensional volume data record taking into account the respective measured and the respective calculated projection images.

The invention claimed is:

1. A method for a separate three-dimensional representation of arteries and/or veins of a vascular system in an examination object based upon a tomography x-ray device, comprising:
   implementing a mask pass of the x-ray device with N projections at N angular positions about the examination object without a contrast agent;
   implementing a first filler pass of the x-ray device about the examination object with M measured projections at M of the N angular positions after an injection of a contrast agent, where M<N;
   implementing a second filler pass of the x-ray device about the examination object with N−M measured projections at N−M of the N angular positions directly following the first filler pass;
   reconstructing a composite three-dimensional volume data record from an intermediate data record, said intermediate data record being determined from the data records resulting from the mask pass, the first filler pass and the second filler pass by subtraction and combination;
   calculating a reprojection data record for arteries by reprojection of the angular positions of the first filler pass from the composite three-dimensional volume data record and/or calculating a reprojection data record for veins by reprojection of the angular positions of the second filler pass from the composite three-dimensional volume data record; and
   calculating a three-dimensional volume data record for arteries and/or a three-dimensional volume data record for veins by weighting the composite three-dimensional volume data record taking into account the respective measured projections and the respective calculated reprojections.

2. The method as claimed in claim 1, wherein M=N/2.

3. The method as claimed in claim 2, wherein every second angular position of the mask pass is used during the first filler pass, the remaining angular positions of the mask pass being used during the second filler pass.

4. The method as claimed in claim 2, wherein the mask pass, the first filler pass and the second filler pass are implemented in the same scan direction.

5. The method as claimed in claim 1, wherein each angular position of the mask pass is used just once either during the first filler pass or during the second filler pass.

6. The method as claimed in claim 5, wherein the mask pass, the first filler pass and the second filler pass are implemented in an alternating manner in different scan directions.

7. The method as claimed in claim 1, wherein each angular position of the mask pass is used just once either during the first filler pass or during the second filler pass.

8. The method as claimed in claim 1, wherein the intermediate data record results from
- a subtraction of part of the data record obtained during the mask pass, in which part the angular positions correspond to those of the first filler pass, from the data record of the first filler pass to form a first data record,
- a subtraction of part of the data record obtained during the mask pass, in which part the angular positions correspond to those of the second filler pass, from the data record of the second filler pass to form a second data record, and
- a combination of the first and second data records.

9. The method as claimed in claim 8, wherein the first filler pass is started at the time of a contrast agent injection into the vessel to be examined and the second filler pass is started at the start of the venous phase.

10. The method as claimed in claim 1, wherein the intermediate data record results from
- a combination of the data record resulting from the first filler pass and the data record resulting from the second filler pass to form a combined data record, and
- a subtraction of the data record resulting from the mask pass from the combined data record taking into account corresponding angular positions.

11. The method as claimed in claim 10, wherein the first filler pass is started at the time of a contrast agent injection into the vessel to be examined and the second filler pass is started at the start of the venous phase.

12. The method as claimed in claim 1, wherein for calculating a three-dimensional volume data record for arteries and/or a three-dimensional volume data record for veins by weighting the composite three-dimensional volume data record taking into account the respective measured projections and the respective calculated reprojections the volume data record for arteries is obtained by multiplying the composite three-dimensional data record by the backprojection of a weighted projection data record for arteries, the weighted projection data record for arteries being formed from the quotients of the individual projection images of the first filler pass with the respective projection images of the reprojection data record for arteries produced for corresponding angular positions.

13. The method as claimed in claim 1, wherein for calculating a three-dimensional volume data record for arteries and/or a three-dimensional volume data record for veins by weighting the composite three-dimensional volume data record taking into account the respective measured projections and the respective calculated reprojections the volume data record for veins is obtained by multiplying the composite three-dimensional data record by the backprojection of a weighted projection data record for veins, the weighted projection data record for veins being formed from the quotients of the individual projection images of the second filler pass with the respective projection images of the reprojection data record for veins produced for corresponding angular positions.

14. The method as claimed in claim 1, wherein for calculating a three-dimensional volume data record for arteries and/or a three-dimensional volume data record for veins by weighting the composite three-dimensional volume data record taking into account the respective measured projections and the respective calculated reprojections the volume data record for arteries is obtained by multiplying the composite three-dimensional data record by the backprojection of the projection images of the first filler pass and then dividing it by the backprojection of the reprojection data record for arteries.

15. The method as claimed in claim 1, wherein for calculating a three-dimensional volume data record for arteries and/or a three-dimensional volume data record for veins by weighting the composite three-dimensional volume data record taking into account the respective measured projections and the respective calculated reprojections the volume data record for veins is obtained by multiplying the composite three-dimensional data record by the backprojection of the projection images of the second filler pass and then dividing it by the backprojection of the reprojection data record for veins.

16. The method as claimed in claim 1, wherein the mask pass, the first filler pass and the second filler pass are implemented in the same scan direction.

17. The method as claimed in claim 1, wherein the mask pass, the first filler pass and the second filler pass are implemented in an alternating manner in different scan directions.

18. The method as claimed in claim 1, wherein the first filler pass is started at the time of a contrast agent injection into the vessel to be examined and the second filler pass is started at the start of the venous phase.

19. A device for a separate three-dimensional representation of arteries and/or veins of a vascular system of an examination object, comprising:
- a tomography x-ray device for:
  - implementing a mask pass with N projections at N angular positions about the examination object without a contrast agent;
  - implementing a first filler pass about the examination object with M measured projections at M of the N angular positions after an injection of a contrast agent, where M<N;
  - implementing a second filler pass about the examination object with N−M measured projections at N−M of the N angular positions directly following the first filler pass; and
- a computer configured to perform:
  - reconstructing a composite three-dimensional volume data record from an intermediate data record, said intermediate data record being determined from the data records resulting from the mask pass, the first filler pass and the second filler pass by subtraction and combination;
  - calculating a reprojection data record for arteries by reprojection of the angular positions of the first filler pass from the composite three-dimensional volume data record and/or calculating a reprojection data record for veins by a reprojection of the angular positions of the second filler pass from the composite three-dimensional volume data record; and
  - calculating a three-dimensional volume data record for arteries and/or a three-dimensional volume data record for veins by weighting the composite three-dimensional volume data record taking into account the respective measured projections and the respective calculated reprojections.

20. The device as claimed in claim 19, wherein the tomography x-ray device is a C-arm x-ray device.

* * * * *